(12) United States Patent
Xie et al.

(10) Patent No.: US 7,399,812 B2
(45) Date of Patent: Jul. 15, 2008

(54) SILICON ETHER COMPOUNDS AND A METHOD FOR THE PREPARATION THEREOF

(75) Inventors: Lunjia Xie, Beijing (CN); Mingzhi Gao, Beijing (CN); Siyuan Zhao, Beijing (CN); Jing Ma, Beijing (CN); Zhufang Sun, Beijing (CN); Haitao Liu, Beijing (CN); Tianyi Li, Beijing (CN); Mingsen Zhang, Beijing (CN); Changjiang Wu, Beijing (CN)

(73) Assignees: China Petroleum & Chemical Corporation, Chaoyang District, Beijing (CN); Beijing Research Institute of Chemical Industry, China Petroleum & Chemical Corporation, Chaoyang District, Beijing (CN)

( * ) Notice: Subject to any disclaimer, the term of this patent is extended or adjusted under 35 U.S.C. 154(b) by 230 days.

(21) Appl. No.: 11/059,581

(22) Filed: Feb. 16, 2005

(65) Prior Publication Data
US 2006/0183873 A1    Aug. 17, 2006

(51) Int. Cl.
C08F 4/42 (2006.01)
(52) U.S. Cl. ............... 526/128; 526/124.2; 526/124.3; 526/351; 526/348; 526/124.6; 502/103; 502/115; 502/118
(58) Field of Classification Search ............ 526/124.2, 526/124.3, 351, 348, 128, 124.6; 502/103, 502/115, 118
See application file for complete search history.

(56) References Cited

U.S. PATENT DOCUMENTS 6,822,109 B2    11/2004    Xie et al.

2006/0142146 A1 *  6/2006  Gao et al. ............ 502/103

FOREIGN PATENT DOCUMENTS

| CN | 1542014 | 11/2004 |
|---|---|---|
| JP | 4-283592 | 10/1992 |
| JP | 7-330656 | 12/1995 |
| JP | 8-198797 | 8/1996 |

OTHER PUBLICATIONS

Hua et al., Chinese Chemical Letters, vol. 15(12), 1430-1432(2004).*
Diekman et al., the Journal of Organic Chemistry, vol. 33(6), 2271-2284(1968).*

* cited by examiner

*Primary Examiner*—Ling-Siu Choi
(74) *Attorney, Agent, or Firm*—Ladas and Parry LLP

(57) ABSTRACT

The present invention relates to silicon ether compounds having a general formula (I), a method for the preparation thereof and use thereof as a component of catalysts for polymerization of olefins. In particular, in propylene polymerization, catalyst systems comprising the silicon ether compounds as external electron donor component exhibit good hydrogen response, and can be used to prepare polymer having high isotacticity at high yield.

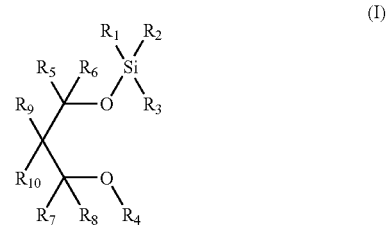

(I)

wherein $R_1$-$R_{10}$ groups are as defined in the description.

15 Claims, No Drawings

SILICON ETHER COMPOUNDS AND A METHOD FOR THE PREPARATION THEREOF

TECHNICAL FIELD

The present invention relates to novel silicon ether compounds, a method for the preparation thereof and use thereof as a component of catalysts for olefins polymerization. In olefins polymerization or copolymerization, in particular, in propylene polymerization or copolymerization, catalyst systems comprising the silicon ether compounds as external electron donor component exhibit good hydrogen response, and can be used to prepare polymer having high isotacticity at high yield.

BACKGROUND ART

Catalysts for olefins polymerization or copolymerization are well known in literatures. These catalysts typically comprise a transition metal-containing active component, generally comprising magnesium, titanium and halogen as main ingredients; a cocatalyst component, typically organo-aluminium compound; and external electron donor component, typically organo-silicon compound. For stereoelective polymerization of olefins, especially stereoelective polymerization of propylene, if no external electron donor component is used, most of these catalysts give a polymer having lower isotacticity, typically lower than 90%, so that they are not applicable to industrial scale production. Therefore, the addition of external electron donor component is often necessary.

At preset, the types of external electron donor compounds have developed from initial benzoates to current organosiloxane. For instance, WO 00/63261 discloses external electron donor compounds useful in olefins polymerization, i.e. silicon compounds having a general formula $R^{11}{}_aR^{12}{}_b Si(OR^{13})_c$, wherein a and b are zero or integer from 1 to 2, c is integer from 1 to 3, and the sum of a+b+c is 4, $R^{11}$, $R^{12}$ and $R^{13}$ are independently $C_1-C_{18}$ hydrocarbyl which optionally contains heteroatom. The preferred are those silicon compounds in which a is 1, b is 1, c is 2, at least one of $R^{11}$ and $R^{12}$ is selected from the group consisting of branched alkyl, alkenyl, alkylene, cycloalkyl and aryl, having from 3 to 10 carbon atoms and containing optionally heteroatom, and $R^{13}$ is $C_1-C_{10}$ alkyl, especially methyl, for example, cyclohexylmethyldimethoxysilane. The also preferred are those silicon compounds in which a is 0, c is 3, $R^{12}$ is branched alkyl or cycloalkyl, containing optionally heteroatom, and $R^{13}$ is methyl, for example, cyclohexyltrimethoxysilane and the like.

It is noted that, among the silicon compounds having the general formula $R^{11}{}_aR^{12}{}_b Si(OR^{13})_c$, those silicon compounds in which c is 1 are generally not deemed as good external electron donor. In the prior art, 2,2-dihydrocarbyl-1-hydrocarbyloxy-3-(trihydrocarbylsilyloxy)propane compounds have never been used as external electron donor compounds in olefins polymerization. However, the inventors have surprisingly found that, when used as external electron donor in olefins polymerization, especially in propylene polymerization, silicon ether compounds of general formula (I), which will be described in detail hereinbelow, exhibit good properties, for instance, the catalyst systems exhibit good hydrogen response, and can be used to prepare polymer having high isotacticity at high yield.

DESCRIPTION THE INVENTION

One object of the present invention is to provide silicon ether compounds having general formula (I):

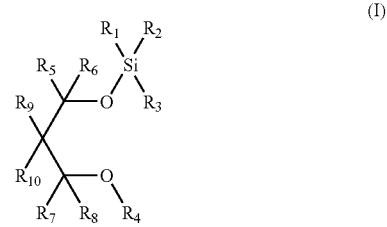

wherein, $R_1-R_4$ groups, which are identical to or different from each other, represent $C_1-C_{20}$ linear or branched, aliphatic, alicyclic or aromatic hydrocarbyl, $R_5-R_{10}$ groups, which are identical to or different from each other, represent hydrogen, halogen, or $C_1-C_{20}$ linear or branched, aliphatic, alicyclic or aromatic hydrocarbyl, and $R_1-R_{10}$ groups optionally contain one or more hetero-atoms selected from the group consisting of nitrogen, oxygen, sulfur, silicon, phosphorus and halogen atom for replacing carbon atom(s), hydrogen atom(s) or the both, with the priviso that when all $R_1-R_3$ are methyl, $R_4$ is not 2-(3-methyl-2-buten-1-yl)-cyclopropan-1-yl;

when $R_1R_2R_3Si$ group represents tert-butyldimethylsilyl or tert-butyldiphenylsilyl, $R_4$ is not benzyl;

when both $R_9$ and $R_{10}$ are hydrogen, $R_5-R_8$ groups are each methyl or hydrogen, and $R_4$ is $C_1-C_4$ linear or branched alkyl, then $R_1-R_3$ are not simultaneously methyl or ethyl; and when both $R_9$ and $R_{10}$ are methyl, all $R_5-R_8$ are hydrogen, and $R_4$ is $C_1-C_3$ linear or branched alkyl, then $R_1-R_3$ are not simultaneously ethyl.

In an embodiment of the invention, in the silicon ether compounds having the general formula (I), $R_1-R_4$ groups, which are identical to or different from each other, represent $C_1-C_{10}$ linear or branched, aliphatic, alicyclic or aromatic hydrocarbyl, and $R_5-R_{10}$ groups, which are identical to or different from each other, represent hydrogen, halogen, or $C_1-C_{10}$ linear or branched, aliphatic, alicyclic or aromatic hydrocarbyl.

In another embodiment of the invention, in the silicon ether compounds having the general formula (I), $R_1-R_4$ groups, which are identical to or different from each other, represent methyl, ethyl, n-propyl, iso-propyl, n-butyl, isobutyl, tert-butyl, phenyl or benzyl, $R_5-R_8$ groups are hydrogen atom, and $R_9$ and $R_{10}$ groups are independently $C_1-C_{10}$ linear or branched, aliphatic, alicyclic or aromatic hydrocarbyl.

In still another embodiment of the invention, the silicon ether compounds according to the invention have general formula (II)

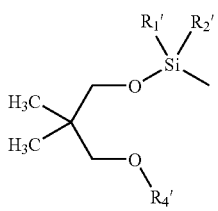

(II)

wherein, $R_1'$-$R_4'$ groups, which are identical to or different from each other, represent linear or branched $C_1$-$C_5$ alkyl, phenyl or benzyl, with the priviso that when $R_1'R_2'R_3'$Si group represents tert-butyldimethylsilyl or tert-butyldiphenylsilyl, $R_4'$ is not benzyl; and when $R_4'$ is $C_1$-$C_3$ linear or branched alkyl, $R_1'$, $R_2'$ and $R_3'$ are not simultaneously ethyl.

Preferably, in the above general formula (II), $R_3'$ and $R_4'$ groups are independently methyl, ethyl, n-propyl, iso-propyl, n-butyl, iso-butyl or tert-butyl.

More preferably, in the above general formula (II), $R_1'$ and $R_2'$ groups are methyl, and $R_3'$ and $R_4'$ groups are independently methyl, ethyl, or tert-butyl. Most preferably, $R_4'$ group is methyl or ethyl.

Examples of the silicon ether compounds of formula (I) include, but are not limited to, 2,2-dimethyl-1-methoxy-3-[(trimethylsilyl)oxy]propane;
2,2-dimethyl-1-methoxy-3-[(triphenylsilyl)oxy]propane;
2,2-dimethyl-1-methoxy-3-[(ethyldimethylsilyl)oxy]propane;
2,2-dimethyl-1-methoxy-3-[(dimethylpropylsilyl)oxy]propane;
2,2-dimethyl-1-methoxy-3-[(tert-butyldimethylsilyl)oxy]propane;
2,2-dimethyl-1-methoxy-3-[(n-butyldimethylsilyl)oxy]propane;
2,2-dimethyl-1-methoxy-3-[(dimethylbenzylsilyl)oxy]propane;
2,2-dimethyl-1-methoxy-3-[(dimethylphenethylsilyl)oxy]propane;
2,2-dimethyl-1-methoxy-3-[(dimethylphenylsilyl)oxy]propane;
2,2-dimethyl-1-methoxy-3-[(dimethyltolylsilyl)oxy]propane;
2,2-dimethyl-1-ethoxy-3-[(trimethylsilyl)oxy]propane;
2,2-dimethyl-1-ethoxy-3-[(triethylsilyl)oxy]propane;
2,2-dimethyl-1-ethoxy-3-[(triphenylsilyl)oxy]propane;
2,2-dimethyl-1-ethoxy-3-[(ethyldimethylsilyl)oxy]propane;
2,2-dimethyl-1-ethoxy-3-[(dimethylpropylsilyl)oxy]propane;
2,2-dimethyl-1-ethoxy-3-[(tert-butyldimethylsilyl)oxy]propane;
2,2-dimethyl-1-ethoxy-3-[(n-butyldimethylsilyl)oxy]propane;
2,2-dimethyl-1-ethoxy-3-[(dimethylbenzylsilyl)oxy]propane;
2,2-dimethyl-1-ethoxy-3-[(dimethylphenethylsilyl)oxy]propane;
2,2-dimethyl-1-ethoxy-3-[(dimethylphenylsilyl)oxy]propane;
2,2-dimethyl-1-ethoxy-3-[(dimethyltolylsilyl)oxy]propane;
2,2-dimethyl-1-propoxy-3-[(trimethylsilyl)oxy]propane;
2,2-dimethyl-1-propoxy-3-[(triethylsilyl)oxy]propane;
2,2-dimethyl-1-propoxy-3-[(triphenylsilyl)oxy]propane;
2,2-dimethyl-1-propoxy-3-[(ethyldimethylsilyl)oxy]propane;
2,2-dimethyl-1-propoxy-3-[(dimethylpropylsilyl)oxy]propane;
2,2-dimethyl-1-propoxy-3-[(tert-butyidimethylsilyl)oxy]propane;
2,2-dimethyl-1-propoxy-3-[(n-butyldimethylsilyl)oxy]propane;
2,2-dimethyl-1-propoxy-3-[(dimethylbenzylsilyl)oxy]propane;
2,2-dimethyl-1-propoxy-3-[(dimethylphenethylsilyl)oxy]propane;
2,2-dimethyl-1-propoxy-3-[(dimethylphenylsilyl)oxy]propane;
2,2-dimethyl-1-propoxy-3-[(dimethyltolylsilyl)oxy]propane;
2,2-di-n-propyl-1-methoxy-3-[(trimethylsilyl)oxy]propane;
2,2-di-iso-butyl-1-methoxy-3-[(trimethylsilyl)oxy]propane;
2,2-di-iso-butyl-1-methoxy-3-[(triethylsilyl)oxy]propane;
2,2-di-iso-butyl-1-methoxy-3-[(triphenylsilyl)oxy]propane;
2,2-di-iso-butyl-1-methoxy-3-[(ethyldimethylsilyl)oxy]propane;
2,2-di-iso-butyl-1-methoxy-3-[(dimethylpropylsilyl)oxy]propane;
2,2-di-iso-butyl-1-methoxy-3-[(tert-butyidimethylsilyl)oxy]propane;
2,2-di-iso-butyl-1-methoxy-3-[(n-butyldimethylsilyl)oxy]propane;
2,2-di-iso-butyl-1-methoxy-3-[(dimethylbenzylsilyl)oxy]propane;
2,2-di-iso-butyl-1-methoxy-3-[(dimethylphenethylsilyl)oxy]propane;
2,2-di-iso-butyl-1-methoxy-3-[(dimethylphenylsilyl)oxy]propane;
2,2-di-iso-butyl-1-methoxy-3-[(dimethyltolylsilyl)oxy]propane;
2,2-di-n-butyl-1-methoxy-3-[(trimethylsilyl)oxy]propane;
2,2-di-n-butyl-1-methoxy-3-[(triethylsilyl)oxy]propane;
2,2-di-n-butyl-1-methoxy-3-[(triphenylsilyl)oxy]propane;
2,2-di-n-butyl-1-methoxy-3-[(ethyldimethylsilyl)oxy]propane;
2,2-di-n-butyl-1-methoxy-3-[(dimethylpropylsilyl)oxy]propane;
2,2-di-n-butyl-1-methoxy-3-[(tert-butyidimethylsilyl)oxy]propane;
2,2-di-n-butyl-1-methoxy-3-[(n-butyldimethylsilyl)oxy]propane;
2,2-di-n-butyl-1-methoxy-3-[(dimethylbenzylsilyl)oxy]propane;
2,2-di-n-butyl-1-methoxy-3-[(dimethylphenethylsilyl)oxy]propane;
2,2-di-n-butyl-1-methoxy-3-[(dimethylphenylsilyl)oxy]propane;
2,2-di-n-butyl-1-methoxy-3-[(dimethyltolylsilyl)oxy]propane;
2,2-di-iso-butyl-1-ethoxy-3-[(trimethylsilyl)oxy]propane;
2,2-di-iso-butyl-1-ethoxy-3-[(triethylsilyl)oxy]propane;

2,2-di-iso-butyl-1-ethoxy-3-[(triphenylsilyl)oxy]propane;
2,2-di-iso-butyl-1-ethoxy-3-[(ethyldimethylsilyl)oxy] propane;
2,2-di-iso-butyl-1-ethoxy-3-[(dimethylpropylsilyl)oxy] propane;
2,2-di-iso-butyl-1-ethoxy-3-[(tert-butyidimethylsilyl) oxy]propane;
2,2-di-iso-butyl-1-ethoxy-3-[(n-butyldimethylsilyl)oxy] propane;
2,2-di-iso-butyl-1-ethoxy-3-[(dimethylbenzylsilyl)oxy] propane;
2,2-di-iso-butyl-1-ethoxy-3-[(dimethylphenethylsilyl) oxy]propane;
2,2-di-iso-butyl-1-ethoxy-3-[(dimethylphenylsilyl)oxy] propane;
2,2-di-iso-butyl-1-ethoxy-3-[(dimethyltolylsilyl)oxy]propane;
2,2-di-iso-butyl-1-propoxy-3-[(trimethylsilyl)oxy]propane;
2,2-di-iso-butyl-1-propoxy-3-[(triethylsilyl)oxy]propane;
2,2-di-iso-butyl-1-propoxy-3-[(triphenylsilyl)oxy]propane;
2,2-di-iso-butyl-1-propoxy-3-[(ethyldimethylsilyl)oxy] propane;
2,2-di-iso-butyl-1-propoxy-3-[(dimethylpropylsilyl)oxy] propane;
2,2-di-iso-butyl-1-propoxy-3-[(tert-butyidimethylsilyl) oxy]propane;
2,2-di-iso-butyl-1-propoxy-3-[(n-butyldimethylsilyl)oxy] propane;
2,2-di-iso-butyl-1-propoxy-3-[(dimethylbenzylsilyl)oxy] propane;
2,2-di-iso-butyl-1-propoxy-3-[(dimethylphenethylsilyl) oxy]propane;
2,2-di-iso-butyl-1-propoxy-3-[(dimethylphenylsilyl)oxy] propane;
2,2-di-iso-butyl-1-propoxy-3-[(dimethyltolylsilyl)oxy] propane;
2,2-dibenzyl-1-methoxy-3-[(trimethylsilyl)oxy]propane;
2,2-dibenzyl-1-methoxy-3-[(triethylsilyl)oxy]propane;
2,2-dibenzyl-1-methoxy-3-[(triphenylsilyl)oxy]propane;
2,2-dibenzyl-1-methoxy-3-[(ethyldimethylsilyl)oxy]propane;
2,2-dibenzyl-1-methoxy-3-[(dimethylpropylsilyl)oxy] propane;
2,2-dibenzyl-1-methoxy-3-[(tert-butyldimethylsilyl)oxy] propane;
2,2-dibenzyl-1-methoxy-3-[(n-butyidimethylsilyl)oxy] propane;
2,2-dibenzyl-1-methoxy-3-[(dimethylbenzylsilyl)oxy] propane;
2,2-dibenzyl-1-methoxy-3-[(dimethylphenethylsilyl)oxy] propane;
2,2-dibenzyl-1-methoxy-3-[(dimethylphenylsilyl)oxy] propane;
2,2-dibenzyl-1-methoxy-3-[(dimethyltolylsilyl)oxy]propane;
2,2-dibenzyl-1-ethoxy-3-[(trimethylsilyl)oxy]propane;
2,2-dibenzyl-1-ethoxy-3-[(triethylsilyl)oxy]propane;
2,2-dibenzyl-1-ethoxy-3-[(triphenylsilyl)oxy]propane;
2,2-dibenzyl-1-ethoxy-3-[(ethyldimethylsilyl)oxy]propane;
2,2-dibenzyl-1-ethoxy-3-[(dimethylpropylsilyl)oxy]propane;
2,2-dibenzyl-1-ethoxy-3-[(tert-butyldimethylsilyl)oxy] propane;
2,2-dibenzyl-1-ethoxy-3-[(n-butyldimethylsilyl)oxy]propane;
2,2-dibenzyl-1-ethoxy-3-[(dimethylbenzylsilyl)oxy]propane;
2,2-dibenzyl-1-ethoxy-3-[(dimethylphenethylsilyl)oxy] propane;
2,2-dibenzyl-1-ethoxy-3-[(dimethylphenylsilyl)oxy]propane;
2,2-dibenzyl-1-ethoxy-3-[(dimethyltolylsilyl)oxy]propane;
2,2-dibenzyl-1-propoxy-3-[(trimethylsilyl)oxy]propane;
2,2-dibenzyl-1-propoxy-3-[(triethylsilyl)oxy]propane;
2,2-dibenzyl-1-propoxy-3-[(triphenylsilyl)oxy]propane;
2,2-dibenzyl-1-propoxy-3-[(ethyldimethylsilyl)oxy]propane;
2,2-dibenzyl-1-propoxy-3-[(dimethylpropylsilyl)oxy] propane;
2,2-dibenzyl-1-propoxy-3-[(tert-butyldimethylsilyl)oxy] propane;
2,2-dibenzyl-1-propoxy-3-[(n-butyldimethylsilyl)oxy] propane;
2,2-dibenzyl-1-propoxy-3-[(dimethylbenzylsilyl)oxy] propane;
2,2-dibenzyl-1-propoxy-3-[(dimethylphenethylsilyl)oxy] propane;
2,2-dibenzyl-1-propoxy-3-[(dimethylphenylsilyl)oxy] propane;
2,2-dibenzyl-1-propoxy-3-[(dimethyltolylsilyl)oxy]propane;

Examples of a preferred group of the the silicon ether compounds of formula (I) include:

2,2-dimethyl-1-methoxy-3-[(trimethylsilyl)oxy]propane;
2,2-dimethyl-1-methoxy-3-[(ethyldimethylsilyl)oxy]propane;
2,2-dimethyl-1-methoxy-3-[(tert-butyidimethylsilyl)oxy] propane;
2,2-dimethyl-1-ethoxy-3-[(trimethylsilyl)oxy]propane;
2,2-dimethyl-1-ethoxy-3-[(ethyldimethylsilyl)oxy]propane;
2,2-dimethyl-1-ethoxy-3-[(tert-butyldimethylsilyl)oxy] propane;
2,2-dimethyl-1-methoxy-3-[(dimethylphenylsilyl)oxy] propane;
2,2-dibenzyl-1-methoxy-3-[(trimethylsilyl)oxy]propane;
2,2-dibenzyl-1-methoxy-3-[(tert-butyldimethylsilyl)oxy] propane;
2,2-di-iso-butyl-1-methoxy-3-[(trimethylsilyl)oxy]propane;
2,2-di-n-butyl-1-methoxy-3-[(trimethylsilyl)oxy]propane;
2,2-di-n-butyl-1-methoxy-3-[(tert-butyidimethylsilyl) oxy]propane;
2,2-di-n-butyl-1-methoxy-3-[(triethylsilyl)oxy]propane;
2,2-di-n-propyl-1-methoxy-3-[(trimethylsilyl)oxy]propane.

Many methods can be used to prepare the silicon ether compounds of the above formula (I), and this constitutes another aspect of the invention.

For instance, a compound of the formula (III)

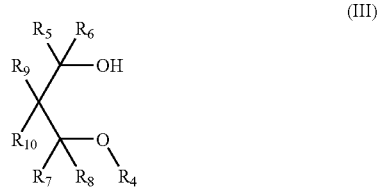

wherein $R_4$ group represents $C_1$-$C_{20}$ linear or branched, aliphatic, alicyclic or aromatic hydrocarbyl, $R_5$-$R_{10}$ groups, which are identical to or different from each other, represent hydrogen, halogen, or $C_1$-$C_{20}$ linear or branched, aliphatic, alicyclic or aromatic hydrocarbyl, and $R_4$-$R_{10}$ groups optionally contain one or more hetero-atoms selected from the group consisting of nitrogen, oxygen, sulfur, silicon, phosphorus and halogen atom for replacing carbon atom(s), hydrogen atom(s) or the both, can react with a trihydrocarbylsilylating agent which can introduce —$SiR_1R_2R_3$ group, wherein $R_1$-$R_3$ groups, which are identical to or different from each other, represent $C_1$-$C_{20}$ linear or branched, aliphatic, alicyclic or aromatic hydrocarbyl, and $R_1$-$R_3$ groups optionally contain one or more heteroatoms selected from the group consisting of nitrogen, oxygen, sulfur, silicon, phosphorus and halogen atom for replacing carbon atom(s), hydrogen atom(s) or the both, in an aprotic inert solvent and, if needed, in the presence of a base, to form corresponding silicon ether compound of the formula (I), wherein equivalent ratio of the compound of formula (III) to the trihydrocarbylsilylating agent is in a range of from 1:1 to 1:1.2.

According to an embodiment of the invention, in the above preparation method, a trihydrocarbylsilyl halide is used as the trihydrocarbylsilylating agent, the reaction of the silylating agent and the compound of fomula (III) is carried out in the presence of a base, and the raw materials are charged at such amounts that molar ratio of the compound of fomula (III): trihydrocarbylsilyl halide:base is in a range of 1:1-1.2:1-1.2. The base used can be selected from the group consisting of inorganic bases and organic bases, such as Na, K, NaOH, KOH, NaH, KH, $CaH_2$, $Na_2CO_3$, $K_2CO_3$, $NH_3$, $Et_3N$, $Me_3N$, $Bu_3N$, pyridine, imidazole, 4-dimethylaminopyridine, and mixture thereof. The preferred are organic bases, such as $Et_3N$, imidazole, and 4-dimethylaminopyridine.

According to another embodiment of the invention, in the above preparation method, a hexahydrocarbyl disilazane is used as the silylating agent, and the raw materials are charged at such amounts that molar ratio of the compound of formula (III) to hexahydrocarbyl disilazane is in a range of 1:0.5-0.6.

The aprotic inert solvent can be selected from the group consisting of amides, halohydrocarbons, hydrocarbons, and ethers, such as dichloromethane, chloroform, benzene, toluene, n-hexane, cyclohexane, petroleum ether, diethyl ether, tetrahydrofuran, tert-butyl methyl ether, N,N-dimethyl formamide, and mixture thereof, with dichloromethane being preferred.

The trihydrocarbylsilylating agent can be selected from the group consisting of trihydrocarbylsilyl halides and hexahydrocarbyl disilazanes, such as trimethylsilyl chloride, ethyldimethylsilyl chloride, tert-butyldimethylsilyl chloride, triethylsilyl chloride, dimethylphenylsilyl chloride, n-butyldimethylsilyl chloride, benzyldimethylsilyl chloride, and hexamethyl disilazane.

The preparation reaction is typically carried out at a temperature of from −20° C. to 100° C., preferably at a lower temperature, more preferably at a temperature of from −5° C. to room temperature.

The compounds of the formula (III) are known in the art or can be synthesized through a method known per se in the art. For instance, said compounds can be obtained through monoetherization of propandiols with haloalkanes. Specifically, a method can comprise the step of mono-etherizing a propandiols compound with a haloalkane in the presence of a solvent and in the presence of a base, to form a 3-hydrocarbyloxy-1-propanol compound, wherein, the solvent used can be selected from the group consisting of tetrahydrofuran, dimethyl sulfoxide, diethyl ether, N,N-dimethyl formamide; aliphatic hydrocarbons, such as, pentane, hexane, and heptane; and aromatic hydrocarbons, such as, benzene, and toluene;

wherein, the base used can be hydrides, hydroxides, or carbonates of alkali metals or alkali earth metals, such as, NaH, KH, $CaH_2$, NaOH, KOH, $Ca(OH)_2$, $Na_2CO_3$, $K_2CO_3$, or the like. Among these bases, NaH and NaOH are preferable. Furthermore, the base is preferably added gradually into the reaction mixture after the addition of the diol, haloalkane and solvent;

and wherein, molar ratio of the base to the propandiols is in a range of from 0.5:1 to 1.5:1, preferably from 0.8:1 to 1.2:1, and molar ratio of the haloalkane to the propandiols is in a range of from 1:1 to 10:1, preferably from 1:1 to 2.5:1.

The present invention further relates to a process for olefins polymerization, wherein a silicon ether compound according to the invention is used as external electron donor compound. In a preferable embodiment, said process is homopolymerization or copolymerization of propylene. Processes for polymerization of olefins and application mode and amount of external electron donor compounds therein are well known in the art.

EMBODIMENTS OF THE INVENTION

The following examples further describe the invention, but do not make limitation to the invention in any way.

Testing Methods:
1. Isotacticity of polymer: measured by heptane extraction method (heptane boiling extraction for 6 hours) carried out according to the following procedure: 2 g of dried polymer sample is extracted with boiling heptane in an extractor for 6 hours, then the residual substance is dried to constant weight, and ratio of the weight of the residual polymer (g) to 2 is taken as isotacticity.
2. Melt index of polymer: measured according to ASTM D1238-99.

Some intermediates used in the Examples were prepared as follows.

Preparation of 2,2-dimethyl-3-methoxy-1-propanol

To a reactor were added 34.4 g of 2,2-dimethyl-1,3-propandiol and 150 ml of dried THF, then 11.3 g of NaH was slowly added with stirring. After the addition, the reaction mixture was refluxed for one hour. Next, a solution of 51.1 g of methyl iodide in 300 ml of THF was added dropwise, and upon completing the addition, the reaction was allowed to continue for further 6 hours. The THF was removed by distillation. The remainder was diluted with 50 ml of water, and extracted thrice with 3×50 ml of diethyl ether. The combined diethyl ether extract was dried over anhydrous magnesium sulfate. After filtering out the magnesium sulfate, diethyl ether was evaporated, and the remainder was distilled under vacuum. 27.7 g of colorless and clear liquid 2,2-dimethyl-3-methoxy-1-propanol (yield 71%) was collected as 86-88° C./71 mmHg fraction.

$^1$H-NMR(CDCl$_3$/TMS, 300 MHz) δ (ppm): 0.91(s, 6H, 2CH$_3$), 2.77 (t, 1H, OH), 3.25(s, 2H, —CH$_2$O—), 3.34(s, 3H, OCH$_3$), 3.44(d, 2H, —CH$_2$O—).

Preparation of 2,2-dimethyl-3-ethoxy-1-propanol

Colorless and clear 2,2-dimethyl-3-ethoxy-1-propanol as 83° C./37 mmHg fraction was prepared from 2,2-dimethyl-1,3-propandiol and ethyl iodide through the same procedure as described in the preparation of 2,2-dimethyl-3-methoxy-1-propanol.

$^1$H NMR (CDCl$_3$/TMS, 300 MHz) δ (ppm): 0.92 (s, 6H, —CH$_3$), 1.19 (t, 3H, —CH$_3$), 2.98 (t, 1H, —OH), 3.29 (s, 2H, —CH$_2$O—), 3.44-3.51 (m, 4H, —OC$\underline{H}_2$CH$_3$, —C$\underline{H}_2$O—).

Preparation of 2,2-dibenzyl-3-methoxy-1-propanol 2,2-Dibenzyl-3-methoxy-1-propanol was prepared from 2,2-dibenzyl-1,3-propandiol and methyl iodide through the same procedure as described above.

$^1$H-NMR(CDCl$_3$/TMS) δ (ppm): 2.34(t, 1H, OH), 2.75(s, 4H, CH$_2$Ph), 3.13(s, 2H, CH$_2$O), 3.33(s, 3H, OCH$_3$), 3.44(d, 2H, CH$_2$O), 7.20(m, 6H, 6ArH), 7.28(m, 4H, 4ArH).

Preparation of 2,2-di-iso-butyl-3-methoxy-1-propanol 2,2-Di-iso-butyl-3-methoxy-1-propanol was prepared from 2,2-di-iso-butyl-1,3-propandiol and methyl iodide through the same procedure as described above.

$^1$H-NMR(CDCl$_3$/TMS) δ (ppm): 0.92(t, 12H, 4CH$_3$), 1.26 (d, 4H, 2CH$_2$), 1.69(m, 2H, 2CH), 2.84(t, 1H, OH), 3.31(2s, 5H, CH$_3$O, CH$_2$O), 3.52(d, 2H, CH$_2$O).

Preparation of 2,2-di-n-butyl-3-methoxy-1-propanol 2,2-Di-n-butyl-3-methoxy-1-propanol was prepared from 2,2-di-n-butyl-1,3-propandiol and methyl iodide through the same procedure as described above.

$^1$H-NMR(CDCl$_3$/TMS) δ (ppm): 0.90(t, 6H, 2CH$_3$), 1.20 (t, 4H, 2CH$_2$), 1.26(m, 8H, 4CH$_2$), 2.75(t, 1H, OH), 3.29(s, 2H, CH$_2$O), 3.32(s, 3H, OCH$_3$), 3.48(d, 2H, CH$_2$O).

Preparation of 2,2-di-n-propyl-3-methoxy-1-propanol 2,2-Di-n-propyl-3-methoxy-1-propanol was prepared from 2,2-di-n-propyl-1,3-propandiol and methyl iodide through the same procedure as described above.

$^1$H-NMR(CDCl$_3$/TMS) δ (ppm): 0.89(t, 6H, 2CH$_3$), 1.24 (m, 8H, 4CH$_2$), 2.70(s, 1H, OH), 3.28(s, 2H, CH$_2$O), 3.32(s, 3H, OCH$_3$), 3.48(s, 2H, CH$_2$O).

EXAMPLE 1

Preparation of 2,2-dimethyl-1-methoxy-3-[(trimethylsilyl)oxy]propane 1 g of 2,2-dimethyl-3-methoxy-1-propanol was dissolved in 20 ml of dichloromethane. The resultant solution was cooled in ice-water bath to below 5° C., and 1.65 ml of triethyl amine was added thereto. After stirring the mixture for 5 minutes, 1.29 ml of trimethylsilyl chloride was added dropwise to the reaction mixture, and the mixture was stirred in ice-water bath for further 2 hours, and at room temperature for further 1 hour. The reaction mixture was washed with water, and the organic layer separated was dried over anhydrous sodium sulfate. After filtration, the filtrate was concentrated to give 1.33 g of concentrate. The crude product was purified by column chromatography using petroleum ether as eluent, to give colorless pure compound.

$^1$H-NMR(CDCl$_3$/TMS) δ (ppm): 0.09(s, 9H, 3CH$_3$), 0.85 (s, 6H, 2CH$_3$), 3.11(s, 2H, —CH$_2$O—), 3.30(s, 2H, —CH$_2$O—), 3.32(s, 3H, CH$_3$O—).

EXAMPLE 2

Preparation of 2,2-dimethyl-1-methoxy-3-[(ethyldimethylsilyl)oxy]-propane

According to the procedure as described in Example 1,2,2-dimethyl-1-methoxy-3-[(ethyldimethylsilyl)oxy]propane was prepared from intermediate 2,2-dimethyl-3-methoxy-1-propanol and reagent ethyldimethylsilyl chloride.

$^1$H-NMR(CDCl$_3$/TMS) δ (ppm): 0.06(s, 6H, 2CH$_3$), 0.54 (q, 2H, CH$_2$), 0.85(s, 6H, 2CH$_3$), 0.95(t, 3H, CH$_3$), 3.11(s, 2H, CH$_2$O), 3.31(2s, 5H, CH$_3$O, CH$_2$O).

EXAMPLE 3

Preparation of 2,2-dimethyl-1-methoxy-3-[(tert-butyldimethylsilyl)oxy]-propane 1 g of 2,2-dimethyl-3-methoxy-1-propanol was admixed with 10 ml of N,N-dimethyl formamide, and 0.29 g of imidazole was added thereto. The mixture was cooled in ice-water bath, and 1.65 ml of triethyl amine was added thereto. After stirring for 5 minutes, 1.65 g of tert-butyldimethylsilyl chloride in 10 ml of N,N-dimethyl formamide was slowly added to the reaction mixture, and the mixture was stirred in ice-water bath for further 4 hours. The reaction mixture was diluted with 10 ml of water, and extracted twice with 20 ml of dichloromethane for each time. The combined dichloromethane extract was dried over anhydrous sodium sulfate. After filtration, the filtrate was evaporated to dryness to give 1.78 g of concentrate of 2,2-dimethyl-1-methoxy-3-[(tert-butyldimethylsilyl)oxy]-propane. The crude product was purified by column chromatography using petroleum ether as eluent, to give colorless pure compound.

$^1$H-NMR(CDCl$_3$/TMS) δ (ppm): 0.01(s, 6H, 2CH$_3$), 0.85 (s, 6H, 2CH$_3$), 0.88(s, 9H, 3CH$_3$), 3.10(s, 2H, CH$_2$O), 3.30 (s, 5H, CH$_2$O, OCH$_3$).

EXAMPLE 4

Preparation of 2,2-dimethyl-1-methoxy-3-[(dimethylphenylsilyl)oxy]-propane

According to the procedure as described in Example 1,2,2-dimethyl-1-methoxy-3-[(dimethylphenylsilyl)oxy]propane was prepared from intermediate 2,2-dimethyl-3-methoxy-1-propanol and reagent dimethylphenylsilyl chloride.

$^1$H-NMR(CDCl$_3$/TMS) δ (ppm): 0.35(s, 6H, 2CH$_3$), 0.87 (s, 6H, 2CH$_3$), 3.13(s, 2H, CH$_2$O), 3.30(s, 3H, OCH$_3$), 3.37 (s, 2H, CH$_2$O), 7.38(m, 3H, 3ArH), 7.58(m, 2H, 2ArH).

EXAMPLE 5

Preparation of 2,2-dimethyl-1-ethoxy-3-[(trimethylsilyl)oxy]propane

According to the procedure as described in Example 1,2,2-dimethyl-1-ethoxy-3-[(trimethylsilyl)oxy]propane was prepared from intermediate 2,2-dimethyl-3-ethoxy-1-propanol and reagent trimethylsilyl chloride.

$^1$H-NMR(CDCl$_3$/TMS) δ (ppm): 0.07(s, 9H, 3CH$_3$), 0.83 (s, 6H, 2CH$_3$), 1.16(t, 3H, CH$_3$), 3.12(s, 2H, CH$_2$O), 3.30(s, 2H, CH$_2$O), 3.43(q, 2H, CH$_2$O).

EXAMPLE 6

Preparation of 2,2-dimethyl-1-ethoxy-3-[(tert-butyidimethylsilyl)oxy]-propane

According to the procedure as described in Example 3,2,2-dimethyl-1-ethoxy-3-[(tert-butyldimethylsilyl)oxy]propane was prepared from intermediate 2,2-dimethyl-3-ethoxy-1-propanol and reagent tert-butyidimethylsilyl chloride.

$^1$H-NMR(CDCl$_3$/TMS) δ (ppm): 0.01 (s, 6H, 2CH$_3$), 0.83 (s, 6H, 2CH$_3$), 0.88(s, 9H, 3CH$_3$), 1.15(t, 3H, CH$_3$), 3.13(s, 2H, CH$_2$O), 3.31(s, 2H, CH$_2$O), 3.43(q, 2H, CH$_2$O).

EXAMPLE 7

Preparation of 2,2-dibenzyl-1-methoxy-3-[(trimethylsilyl)oxy]propane

According to the procedure as described in Example 1,2,2-dibenzyl-1-methoxy-3-[(trimethylsilyl)oxy]propane was prepared from intermediate 2,2-dibenzyl-3-methoxy-1-propanol and reagent trimethylsilyl chloride.

$^1$H-NMR(CDCl$_3$/TMS) δ (ppm): 0.17(s, 9H, 3CH$_3$), 2.72-2.82(dd, 4H, 2CH$_2$), 2.81(s, 2H, CH$_2$O), 3.10(s, 2H, CH$_2$O), 3.46(s, 3H, OCH$_3$), 7.22(m, 6H, 6ArH), 7.29(q, 4H, 4ArH).

EXAMPLE 8

Preparation of 2,2-dibenzyl-1-methoxy-3-[(tert-butyidimethylsilyl)oxy]-propane 4.16 Mmol of 2,2-dibenzyl-3-methoxy-1-propanol was dissolved in 10 ml of N,N-dimethyl formamide, and 0.14 g (2.08 mmol) of imidazole was added thereto. The solution was cooled in ice-water bath to below 5° C., and 0.87 ml (6.24 mmol) of triethyl amine was added thereto. After stirring for 5 minutes, 0.88 g (5.82 mmol) of tert-butyldimethylsilyl chloride in 10 ml of N,N-dimethyl formamide was slowly added to the reaction mixture, and the mixture was stirred in ice-water bath for further 2 hours, and at room temperature for further 1 hour. The reaction mixture was diluted with 10 ml of water, and extracted using 30 ml of dichloromethane. The organic layer was separated, wished twice with 20 ml of water, and dried over anhydrous sodium sulfate. After filtration, the filtrate was concentrated to give 2,2-dibenzyl-1-methoxy-3-[(tert-butyldimethylsilyl)oxy]propane.

$^1$H-NMR(CDCl$_3$/TMS) δ (ppm): 0.07(s, 6H, 2CH$_3$), 1.01 (S, 9H, 3CH$_3$), 2.68-2.79(dd, 4H, 2CH$_2$), 2.83(s, 2H, CH$_2$O), 3.18(s, 2H, CH$_2$O), 3.31(s, 3H, OCH$_3$), 7.25(m, 10H, 10ArH).

EXAMPLE 9

Preparation of 2,2-di-iso-butyl-1-methoxy-3-[(trimethylsilyl)oxy]-propane

According to the procedure as described in Example 1,2,2-di-iso-butyl-1-methoxy-3-[(trimethylsilyl)oxy]propane was prepared from intermediate 2,2-di-iso-butyl-3-methoxy-1-propanol and reagent trimethylsilyl chloride.

$^1$H-NMR(CDCl$_3$/TMS) δ (ppm): 0.06(s, 9H, 3CH$_3$), 0.89 (d, 6H, 2CH$_3$), 0.90(d, 6H, 2CH$_3$), 1.16(d, 2H, CH$_2$), 1.18(d, 2H, CH$_2$), 1.68(m, 2H, 2CH), 3.12(s, 2H, CH$_2$O), 3.26(s, 3H, OCH$_3$), 3.47(s, 2H, CH$_2$O).

EXAMPLE 10

Preparation of 2,2-di-n-butyl-1-methoxy-3-[(trimethylsilyl)oxy]propane

According to the procedure as described in Example 1,2,2-di-n-butyl-1-methoxy-3-[(trimethylsilyl)oxy]propane was prepared from intermediate 2,2-di-n-butyl-3-methoxy-1-propanol and reagent trimethylsilyl chloride.

$^1$H-NMR(CDCl$_3$/TMS) δ (ppm): 0.07(s, 9H, 3CH$_3$), 0.89 (t, 6H, 2CH$_3$), 1.17(m, 8H, 4CH$_2$), 1.26(m, 4H, 2CH$_2$), 3.11 (s, 2H, CH$_2$O), 3.28(s, 3H, OCH$_3$), 3.31 (s, 2H, CH$_2$O).

EXAMPLE 11

Preparation of 2,2-di-n-butyl-1-methoxy-3-[(tert-butyidimethylsilyl)oxy]-propane According to the procedure as described in Example 8,2,2-di-n-butyl-1-methoxy-3-[(tert-butyldimethylsilyl)oxy] propane was prepared from intermediate 2,2-di-n-butyl-3-methoxy-1-propanol and reagent tert-butyidimethylsilyl chloride.

$^1$H-NMR(CDCl$_3$/TMS) δ (ppm): 0.02(s, 6H, 2CH$_3$), 0.88 (s, 9H, 3CH$_3$), 0.91(t, 6H, 2CH$_3$), 1.17(m, 8H, 4CH$_2$), 1.27 (m, 4H, 2CH$_2$), 3.12(s, 2H, CH$_2$O), 3.30(s, 3H, OCH$_3$), 3.34 (s, 2H, CH$_2$O).

EXAMPLE 12

Preparation of 2,2-di-n-butyl-1-methoxy-3-[(triethylsilyl)oxy]propane

According to the procedure as described in Example 1,2,2-di-n-butyl-1-methoxy-3-[(triethylsilyl)oxy]propane was prepared from intermediate 2,2-di-n-butyl-3-methoxy-1-propanol and reagent triethylsilyl chloride.

$^1$H-NMR(CDCl$_3$/TMS) δ (ppm): 0.57(q, 6H, 3CH$_2$), 0.91 (t, 6H, 2CH$_3$), 0.96(t, 9H, 3CH$_3$), 1.20(m, 8H, 4CH$_2$), 1.27 (m, 4H, 2CH$_2$), 3.14(s, 2H, CH$_2$O), 3.30(s, 3H, OCH$_3$), 3.36 (s, 2H, CH$_2$O).

EXAMPLE 13

Preparation of 2,2-di-n-propyl-1-methoxy-3-[(trimethylsilyl)oxy]-propane

According to the procedure as described in Example 1,2,2-di-n-propyl-1-methoxy-3-[(trimethylsilyl)oxy]propane was prepared from intermediate 2,2-di-n-propyl-3-methoxy-1-propanol and reagent trimethylsilyl chloride.

$^1$H-NMR(CDCl$_3$/TMS) δ (ppm): 0.07(s, 9H, 3CH$_3$), 0.88 (t, 6H, 2CH$_3$), 1.17(m, 8H, 4CH$_2$), 3.11(s, 2H, CH$_2$O), 3.28(s, 3H, OCH$_3$), 3.32(s, 2H, CH$_2$O).

EXAMPLES 14-21 AND COMPARATIVE EXAMPLE 1

Preparation of the Solid Titanium-Containing Catalyst Component

To a reactor that had been completely purged with highly pure N$_2$ were added successively 4.8 g of magnesium dichloride, 95 ml of toluene, 4 ml of epichlorohydrin, and 12.5 ml of tributyl phosphate. With stirring, the mixture was heated to 50° C. and held at that temperature for 2.5 hours, thereby the solid was completely dissolved. Then 1.4 g of phthalic anhydride was added thereto and the reaction mixture was held at that temperature with stirring for further one hour. The reaction mixture was cooled to below −25° C. and 56 ml of TiCl$_4$ was added dropwise thereto over one hour, then the temperature was increased slowly to 80° C. Solid precipitated gradually during the heating. To the reaction mixture was added 6 mmol of di-n-butyl phthalate, and the reaction was held at that temperature with stirring for further one hour. After filtering, 70 ml of toluene was used to wash the filter cake. The washing procedure was repeated twice. The resulting solid precipitate was treated with 60 ml of toluene and 40 ml of TiCl$_4$ at 100° C. for 2 hours, and after removing the mother liquid, the residue was treated with 60 ml of toluene and 40 ml of TiCl$_4$ at 100° C. for 2 hours again. After removing the mother liquid, the residue was washed with 60 ml of toluene under boiling state for three times, washed with 60 ml of hexane under boiling state for two times, washed with 60 ml of hexane at room temperature for two times, to yield the solid titanium-containing catalyst component.

Propylene Polymerization Experiments

To a 5L stainless steel autoclave, in which atmosphere had been replaced with propylene gas completely, were added 2.5 mmol of AlEt$_3$, 0.1 mmol of silicon ether compounds prepared in above Examples or known cyclohexylmethyldimethoxysilane, 10 mg of the solid titanium-containing catalyst component prepared above, and 1 L of hydrogen, followed by introduction of 2.3 L of liquid propylene. The reactor was heated to 70° C., and held at that temperature for 1 hour. After the temperature was reduced and the pressure was relieved, PP resin powder was removed. Polymerization results were summarized in Table 1.

TABLE 1

| Example No. | Silicon Ether Compound | Polymerization Activity kgPP/ gcat · h | Isotacticity % | MI |
| --- | --- | --- | --- | --- |
| Example 14 | 2,2-dimethyl-1-methoxy-3-[(trimethylsilyl)oxy]propane | 27.7 | 96.7 | 2.6 |
| Example 15 | 2,2-dimethyl-1-methoxy-3-[(tert-butyldimethylsilyl)oxy]propane | 38.3 | 98.4 | 5.8 |
| Example 16 | 2,2-dimethyl-1-ethoxy-3-[(trimethylsilyl)oxy]propane | 32.0 | 96.8 | 4.8 |
| Example 17 | 2,2-dibenzyl-1-methoxy-3-[(tert-butyldimethylsilyl)oxy]propane | 22.0 | 96.9 | 3.0 |
| Example 18 | 2,2-di-n-butyl-1-methoxy-3-[(trimethylsilyl)oxy]propane | 32.5 | 96.3 | 5.1 |
| Example 19 | 2,2-di-n-butyl-1-methoxy-3-[(tert-butyldimethylsilyl)oxy]propane | 33.7 | 96.3 | 4.6 |
| Example 20 | 2,2-di-n-butyl-1-methoxy-3-[(triethylsilyl)oxy]propane | 35.6 | 96.8 | 6.2 |
| Example 21 | 2,2-di-n-propyl-1-methoxy-3-[(trimethylsilyl)oxy]propane | 25.5 | 96.4 | 5.2 |
| Comparative Example 1 | cyclohexylmethyldimethoxysilane | 34.8 | 98.3 | 3.2 |

EXAMPLE 22 AND COMPARATIVE EXAMPLE 2

Propylene polymerization experiments were carried out according to the same polymerization procedure as described above, except for that the amount of hydrogen gas was changed to 4 L. Polymerization results were summarized in Table 2. For comparison, the results obtained in Example 15 as well as in Comparative Example 1 were also shown in Table 2.

TABLE 2

| Example No. | External Electron Donor | H$_2$ (L) | Polymerization Activity (kgPP/ gcat · h) | Isotacticity % | MI |
| --- | --- | --- | --- | --- | --- |
| Example 15 | 2,2-dimethyl-1-methoxy-3-[(tert-butyldimethyl-silyl)oxy]propane | 1 | 38.3 | 98.4 | 5.8 |
| Example 22 | 2,2-dimethyl-1-methoxy-3-[(tert-butyldimethyl-silyl)oxy]propane | 4 | 47.0 | 97.2 | 27.5 |
| Comparative Example 1 | cyclohexylmethyl-dimethoxysilane | 1 | 34.8 | 98.3 | 3.2 |
| Comparative Example 2 | cyclohexylmethyl-dimethoxysilane | 4 | 44.6 | 97.8 | 19.2 |

From the results shown in Tables 1 and 2, it can be seen that, when the silicon ether compounds according to the present invention are used as external electron donor component of a catalyst for olefin polymerization, polymerization activity of the catalyst and isotacticity of the polymerization product obtained are satisfied. Furthermore, at the same hydrogen gas level, the polymerization using the silicon ether compounds according to the invention will give polymers having higher melt index than the polymerization using the silane compound commonly used in the art, and as the level of hydrogen gas increases, melt index increases more notably. These results sufficiently demonstrate that, when the silicon ether compounds according to the present invention are used as external electron donor component of a catalyst for olefin polymerization, the catalyst will exhibit relatively good hydrogen response, and this performance facilitates the development of various grades of polymers.

The invention aims to develop novel external electron donor compounds useful in propylene polymerization. It is generally accepted that trihydrocarby-hydrocarbyloxy-silanes are not good external electron donors for olefin polymerization, and are not suitable for enhancing isotacticity of the polyolefin product. However, the inventors have found that, when using preferred silicon ether compounds of the invention substituting for cyclohexylmethyldimethoxysilane known in the art as external electron donor in olefin polymerization, a current catalyst remains its high catalytic activity, and exhibits good hydrogen response, and the prepared polypropylene has high isotacticity. These results prove that the silicon ether compounds of the invention are a class of highly effective external electron donor compounds.

Although the present invention has been described in connection with embodiments and examples, further modifications and alternative embodiments of various aspects of the invention will be apparent to those skilled in the art in view of this description. Accordingly, this description is to be constructed as illustrative only and is for the purpose of teaching the general manner of carrying out the invention.

What is claimed is:

1. A silicon ether compound having a general formula (I):

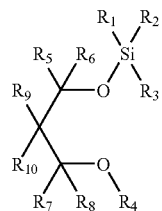

(I)

wherein, $R_1$-$R_4$ groups, which are identical to or different from each other, represent $C_1$-$C_{20}$ linear or branched, aliphatic, alicyclic or aromatic hydrocarbyl, $R_5$-$R_8$ groups, which are identical to or different from each other, represent hydrogen, halogen, or $C_1$-$C_{20}$ linear or branched, aliphatic, alicyclic or aromatic hydrocarbyl, $R_9$ and $R_{10}$ groups, which are identical to or different from each other represent halogen, or $C_1$-$C_{20}$ linear or branched, aliphatic, alicyclic or aromatic hydrocarbyl, and $R_1$-$R_{10}$ groups optionally contain one or more hetero-atoms selected from the group consisting of nitrogen, oxygen, sulfur, silicon, phosphorus and halogen atom for replacing carbon atom(s), hydrogen atom(s) or the both, with the priviso that when all $R_1$-$R_3$ groups are methyl, $R_4$ is not 2-(3-methyl-2-buten-1-yl)-cyclopropan-1-yl;

when $R_1R_2R_3$Si group represents tert-butyldimethylsilyl or tert-butyldiphenylsilyl, $R_4$ is not benzyl; and when both $R_9$ and $R_{10}$ are methyl, all $R_5$-$R_8$ groups are hydrogen, and $R_4$ is $C_1$-$C_3$ linear or branched alkyl, then $R_1$-$R_3$ groups are not simultaneously ethyl.

2. The silicon ether compound of the formula (I) according to claim 1, wherein $R_1$-$R_4$ groups, which are identical to or different from each other, represent $C_1$-$C_{10}$ linear or branched, aliphatic, alicyclic or aromatic hydrocarbyl, and $R_5$-$R_8$ groups, which are identical to or different from each other, represent hydrogen, halogen, or $C_1$-$C_{10}$ linear or branched, aliphatic, alicyclic or aromatic hydrocarbyl, and $R_9$-$R_{10}$ groups, which are identical to or different from each other, represent halogen, or $C_1$-$C_{10}$ linear or branched, aliphatic, alicyclic or aromatic hydrocarbyl.

3. The silicon ether compound of the formula (I) according to claim 1, wherein $R_1$-$R_4$ groups, which are identical to or different from each other, represent methyl, ethyl, n-propyl, iso-propyl, n-butyl, isobutyl, tert-butyl, phenyl or benzyl, $R_5$-$R_8$ groups are hydrogen atom, and $R_9$ and $R_{10}$ groups are independently $C_1$-$C_{10}$ linear or branched, aliphatic, alicyclic or aromatic hydrocarbyl.

4. The silicon ether compound according to claim 1, having a general formula (II):

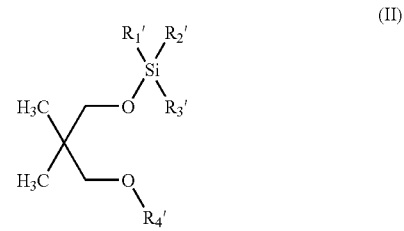

(II)

wherein, $R_1'$-$R_4'$ groups, which are identical to or different from each other, represent linear or branched $C_1$-$C_5$ alkyl, phenyl or benzyl, with the priviso that when $R_1'R_2'R_3'$Si group represents tert-butyldimethylsilyl or tert-butyldiphenylsilyl, $R_4'$ is not benzyl; and when $R_4'$ is $C_1$-$C_3$ linear or branched alkyl, then $R_1'$, $R_2'$ and $R_3'$ are not simultaneously ethyl.

5. The silicon ether compound according to claim 4, wherein $R_3'$ and $R_4'$ groups are independently methyl, ethyl, n-propyl, iso-propyl, n-butyl, iso-butyl or tert-butyl.

6. The silicon ether compound according to claim 4, wherein $R_1'$ and $R_2$ groups are methyl, and $R_3'$ and $R_4'$ groups are independently methyl, ethyl, or tert-butyl.

7. The silicon ether compound according to claim 6, wherein $R_4'$ group is methyl or ethyl.

8. The silicon ether compound according to claim 1, seleted from the group consisting of 2,2-dimethyl-1-methoxy-3-[(trimethylsilyl)oxy]propane;

2,2-dimethyl-1-methoxy-3-[(ethyldimethylsilyl)oxy]propane;

2,2-dimethyl-1-methoxy-3-[(tert-butyldimethylsilyl)oxy] propane;

2,2-dimethyl-1-methoxy-3-[(dimethylphenylsilyl)oxy] propane;

2,2-dimethyl-1-ethoxy-3-[(trimethylsilyl)oxy]propane;

2,2-dimethyl-1-ethoxy-3-[(ethyldimethylsilyl)oxy]propane;

2,2-dimethyl-1-ethoxy-3-[(tert-butyldimethylsilyl)oxy] propane 2,2-dibenzyl-1-methoxy-3-[(trimethylsilyl)oxy]propane;

2,2-dibenzyl-1-methoxy-3-[(tert-butyldimethylsilyl)oxy] propane 2,2-di-iso-butyl-1-methoxy-3-[(trimethylsilyl)oxy]propane;

2,2-di-n-butyl-1-methoxy-3-[(trimethylsilyl)oxy]propane;

2,2-di-n-butyl-1-methoxy-3-[(tert-butyldimethylsilyl) oxy]propane 2,2-di-n-butyl-1-methoxy-3-[(triethylsilyl)oxy]propane;

2,2-di-n-propyl-1-methoxy-3-[(trimethylsilyl)oxy]propane.

9. A method for the preparation of the silicon ether compound according to claim 1, comprising the step of:

reacting a compound of the formula (III)

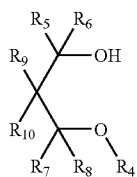

wherein $R_4$-$R_{10}$ groups are as defined in claim 1, with a trihydrocarbylsilylating agent which can introduce —$SiR_1R_2R_3$ group,
wherein $R_1$, $R_2$ and $R_3$ groups are as defined in claim 1, in an aprotic inert solvent and, if needed, in the presence of a base, to form corresponding silicon ether compound of the formula (I), wherein equivalent ratio of the compound of formula (III) to the trihydrocarbylsilylating agent is in a range of from 1:1 to 1:1.2.

10. The method according to claim 9, wherein the aprotic inert solvent is selected from the group consisting of dichloromethane, chloroform, benzene, toluene, n-hexane, cyclohexane, petroleum ether, diethyl ether, tetrahydrofuran, tert-butyl methyl ether, N,N-dimethyl formamide, and mixture thereof.

11. The method according to claim 9, wherein a trihydrocarbylsilyl halide is used as the trihydrocarbylsilylating agent, the reaction of the silylating agent and the compound of fomula (III) is carried out in the presence of a base, and the raw materials are charged at such amounts that molar ratio of the compound of fomula (III): trihydrocarbylsilyl halide : base is in a range of 1:1-1.2:1-1.2.

12. The method according to claim 11, wherein the base is selected from the group consisting of Na, K, NaOH, KOH, NaH, KH, $CaH_2$, $Na_2CO_3$, $K_2CO_3$, $NH_3$, $Et_3N$, $Me_3N$, $Bu_3N$, pyridine, imidazole, 4-dimethylaminopyridine, and mixture thereof.

13. The method according to claim 9, wherein a hexahydrocarbyl disilazane is used as the silylating agent, and the raw materials are charged at such amounts that molar ratio of the compound of formula (III) to hexahydrocarbyl disilazane is in a range of 1:0.5-0.6.

14. A process comprising polymerizing olefins, with the silicon ether compound according to claim 1 as an external electron donor compound.

15. The process according to claim 14, wherein said process is homopolymerization or copolymerization of propylene.

* * * * *